United States Patent [19]

Iga et al.

[11] Patent Number: 5,252,336
[45] Date of Patent: Oct. 12, 1993

[54] LIPOSOME COMPOSITION WHOSE LIPOSOME MEMBRANE CONTAINS A POLYOXYETHYLENE DERIVATIVE

[75] Inventors: Katsumi Iga, Suita; Kazuhiro Ohkouchi, Osaka; Yasuaki Ogawa, Otokuni, all of Japan

[73] Assignee: Takeda Chemical Industries, Ltd., Osaka, Japan

[21] Appl. No.: 687,918

[22] PCT Filed: Apr. 12, 1991

[86] PCT No.: PCT/JP91/00481
§ 371 Date: Jun. 5, 1991
§ 102(e) Date: Jun. 5, 1991

[87] PCT Pub. No.: WO91/16040
PCT Pub. Date: Oct. 31, 1991

[30] Foreign Application Priority Data
Apr. 18, 1990 [JP] Japan .................. 2-103902

[51] Int. Cl.$^5$ ............................. A61K 9/127
[52] U.S. Cl. ................... 424/450; 424/420; 428/402.2; 436/829
[58] Field of Search ............ 424/450, 417, 420; 436/829; 428/402.2

[56] References Cited

U.S. PATENT DOCUMENTS

| | | | |
|---|---|---|---|
| 4,411,882 | 10/1983 | Franz | 424/450 |
| 4,844,904 | 7/1989 | Hamaguchi | 424/450 |
| 5,019,394 | 5/1991 | Hamaguchi | 424/423 |
| 5,028,606 | 7/1991 | Venet | 514/249 |

FOREIGN PATENT DOCUMENTS

| | | |
|---|---|---|
| 0102324 | 3/1984 | European Pat. Off. . |
| 0220797 | 5/1987 | European Pat. Off. . |
| 0280492 | 8/1988 | European Pat. Off. . |
| 2552666 | 4/1985 | France . |
| 0149531 | 8/1985 | Japan . |

Primary Examiner—Thurman K. Page
Assistant Examiner—G. S. Kishore
Attorney, Agent, or Firm—Wenderoth, Lind & Ponack

[57] ABSTRACT

A liposome composition is obtained by using as constituent components of the liposome membrane a polyoxyethylene derivative represented by the general formula:

$$X-O-(CH_2CH_2O)_n-Y \quad (I)$$

wherein X represents an alkanoyl group or an alkyl group, Y represents a residue of a compound having a negative charge, and n is an integer of 2 to 50, and a phospholipid. The liposome composition has good dispersibility, high drug-encapsulation property and high stability.

5 Claims, 2 Drawing Sheets

LIPOSOME COMPOSITION WHOSE LIPOSOME MEMBRANE CONTAINS A POLYOXYETHYLENE DERIVATIVE

DESCRIPTION

Technical Field

The present invention relates to a liposome composition.

Background Art

In general, among drugs which are effective in vitro, many of them disappear before sufficient manifestation of their activities at target sites due to rapid metabolism thereof after administration in vivo. As means for making such drugs more effective at target sites, various drug delivery systems (DDS) have been studied. In particular, DDS wherein a drug is encapsulated in liposome is useful for lasting blood level of the drug and targeting the drug toward a specific site and, therefore, it is considered to be an effective preparation. However, such liposome does not always manifest its function as DDS sufficiently after administration, and its function largely depends on the manufacturing conditions of the liposome and a particular kind of lipid used as the liposome membrane component.

As the major problems of liposome, encapsulation efficiency of a drug, stability of a liposome membrane for maintaining the encapsulated drug for a long period of time, and dispersibility of liposome are pointed out. In general, liposome prepared by using a lipid such as phospholipid or the like as the liposome membrane component is poor in dispersibility, which causes aggregation in a short period of time and often adversely affects the drug encapsulation properties and stability of the liposome. Such liposome is often incorporated in reticulo-endothelial system (RES) at an earlier stage after administration, which results in failure to manifest its function as DDS.

Accordingly, for the development of DDS using liposome, it is of importance to improve dispersibility to produce stable liposome.

OBJECTS OF THE INVENTION

The development of liposome with good dispersibility, high encapsulation property and higher stability by modification of the composition of a liposome membrane is not yet sufficient.

In view of these circumstances, the present inventors have studied intensively to obtain liposome with good dispersibility, high encapsulation property and higher stability by modification of the composition of the liposome membrane aiming at addition of a membrane modification component to the composition of the membrane.

Thus, the main object of the present invention is to provide novel liposome with good dispersibility, high encapsulation property and higher stability.

This object as well as other objects and advantages of the present invention will be apparent to those skilled in the art from the following description with reference to the accompanying drawings.

SUMMARY OF THE INVENTION

Figure 1:
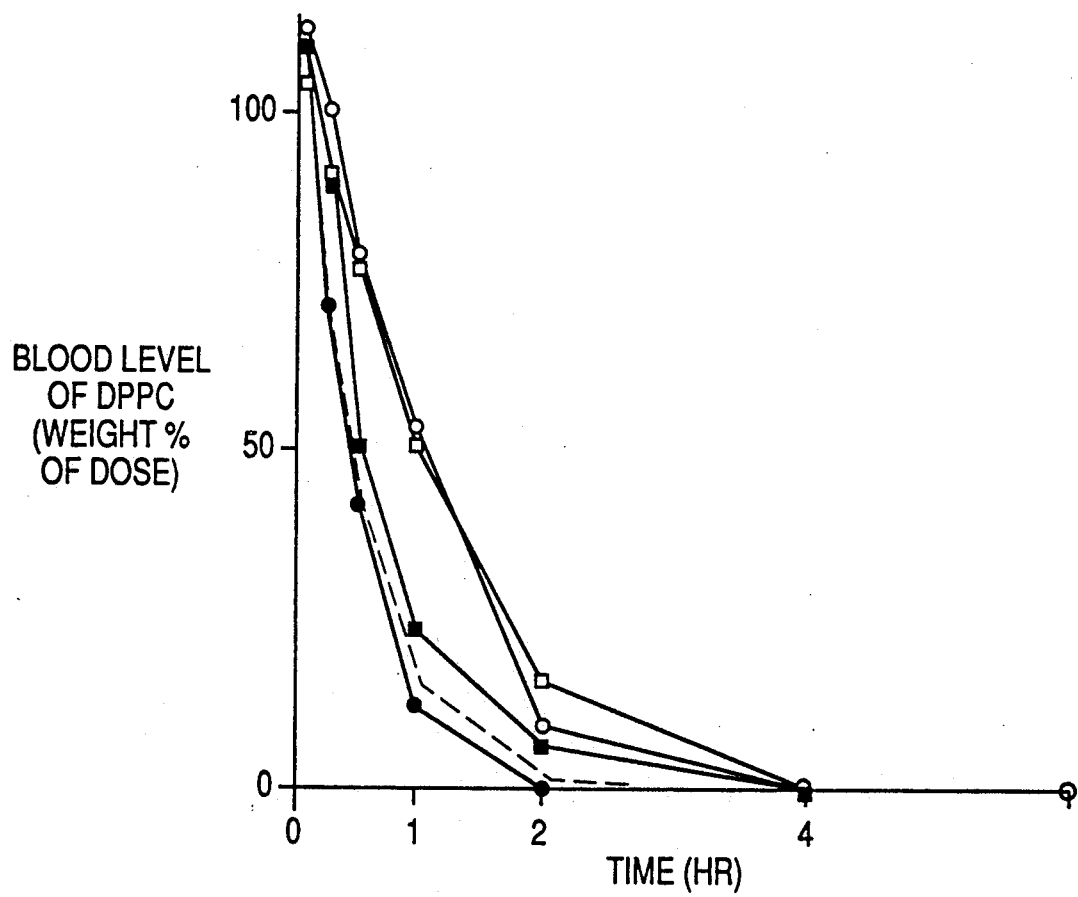
FIG. 1 shows change of blood level of lipid after administration of the liposome compositions shown in Experiment 4 hereinafter, wherein ■, ●, O, □ and --- represent the liposome compositions of Examples 2, 3, 4 and 5 as well as Sample 1 hereinafter, respectively.

The present invention provides a liposome composition whose liposome membrane comprises a polyoxyethylene derivative represented by the general formula:

$$X-O-(CH_2CH_2O)_n-Y \quad (I)$$

wherein X represents an alkanoyl group or an alkyl group, Y represents an anion-forming group, and n is an integer of 2 to 50, and a phospholipid.

DETAILED DESCRIPTION OF THE INVENTION

Regarding the above polyoxyethylene derivative, the alkanoyl group represented by X is preferably $C_{5-30}$ straight or branched chain alkylcarbonyl and examples thereof include valeryl, isovaleryl, pivaloyl, lauroyl, myristoyl, palmitoyl, stearoyl and the like. Among them, $C_{12-20}$ straight-chain alkanoyl groups are especially preferred. The alkyl group represented by X is preferably $C_{5-30}$ straight or branched chain alkyl and examples thereof include pentyl, hexyl, octyl, decyl, dodecyl (lauryl), tridecyl, hexadecyl (cetyl), octadecyl, eicosyl and the like. Particularly, straight-chain $C_{12-20}$ alkyl groups are preferred.

The number of polyoxyethylene units represented by the integer n is preferably 2 to 30.

The anion-forming group represented by Y includes, for example, a residue of a compound having a negative charge such as acetic acid residue ($-CH_2CO_2H$), propionic acid residue ($CH_2CH_2CO_2H$), sulfuric acid residue ($-OSO_3H$), sulfonic acid residue ($-CH_2SO_3H$, $-CH_2CH_2SO_3H$ etc.), phosphoric acid residue ($-O-PO_3H$) and the like. The anion-forming group may form salts such as those with an alkali metal (e.g., potassium, sodium, etc.), an alkaline earth metal (e.g., calcium, magnesium, etc.) and the like.

The aforementioned polyoxyethylene derivative per se is a known material and commercially available or can be produced from known materials according to known methods.

As the phospholipid used for the liposome composition of the present invention, naturally occurring or semi-synthesized, or totally synthesized phospholipid can be used. Examples of the naturally occurring phospholipid include glycerophospholipid such as egg yolk lecithine, soybean lecithine, or sphingophospholipid. As the semi-synthesized or totally synthesized phospholipid, glycerophospholipid or sphingophospholipid wherein the alkanoyl group is a saturated or a partially unsaturated alkanoyl group can be used. Preferably, glycerophospholipid or sphingophospholipid having a saturated alkanoyl group is used. The number of carbon atoms in the saturated alkanoyl group is preferably 12 to 20.

In the present invention, the liposome membrane comprises as constituent components the above phospholipid and polyoxyethylene derivative.

The ratio of the phospholipid to the polyoxyethylene derivative used in the present invention is generally about 0.5 to 200 parts by weight, preferably about 2 to 50 parts by weight, more preferably, 5 to 20 parts by weight of the polyoxyethylene derivative based on 100 parts by weight of the phospholipid.

The present invention is characterized by using the aforementioned phospholipid and polyoxyethylene derivative as constituent components of the liposome membrane and, in order to produce the liposome composition, any known technique can be employed. For example, constituent components of the liposome membrane including the above glycerophospholipid and polyoxyethylene derivative are dissolved in an organic solvent such as diethyl ether, isopropyl ether, chloroform or the like, to which is further added an aqueous solution of a drug. The resulting mixture is emulsified to obtain a W/O type emulsion, from which the organic solvent is removed by evaporation at a suitable temperature (slightly higher than the phase transition temperature) under reduced pressure to obtain reverse phase evaporation vesicles (REV). In another process, the above solution of lipid in the organic solvent is evaporated under reduced pressure to remove the organic solvent to form a thin film and then the drug solution is admixed with the resulting mixture at the aforementioned temperature to obtain multi-lamellar vesicles (MLV). Further, the MLV is shaken in a probe type ultrasonic shaker to obtain small uni-lamellar vesicles (USV). Other processes for the production of liposome include stable plurilamellar vesicle (SPLV) process (Japanese Patent Laid-Open Publication No. 500952/1984) and dehydration rehydration vesicle process [C. Kirby et al., Biotechnology, Nov., 979 (1984)]. The polyoxyethylene derivative may be dispersed in a solution of a drug instead of dissolution in an organic solvent as described above. In still another process, liposome in which a drug is encapsulated by the phospholipid is prepared, then, the resultant is added to a dispersion containing the phospholipid and the mixture is mixed with heating to arrange the polyoxyethylene derivative in the previously formed liposome membrane.

Regarding a fat-soluble drug with low solubility in water, the liposome in which a drug is encapsulated can be obtained by dissolving the drug in the above solution of lipid in the organic solvent. Optionally, the liposome thus obtained encapsulating the drug can be adjusted to the desired particle size. The resulting liposome may be used as it is. However, preferably, the liposome is used after removing free drug which is not encapsulated by centrifugation, gel filtration or dialysis. Examples of the drugs used in the present invention include carcinostatic agents such as cisplatin, adriamycin, mitomycin C, actinomycin, ansamitocin, bleomycin, 5-FU and methotrexate; lymphokines such as naturally occurring or genetic recombinant type interferon ($\alpha$, $\beta$, $\gamma$), and naturally occurring or genetic recombinant type interleukin 2; physiologically active peptides such as manganese superoxide dismutase (SOD) and derivatives thereof such as superoxide dismutase PEG (PEG-5000) (Japanese Patent Laid-Open Publication No. 132658/1982); $\beta$-lactam antibiotics such as sulfazecin; aminoglycoside antibiotics such as gentamicin, streptomycin and kanamycin; vitamins such as cyanocobalamin and ubiquinone; antiprotozoal such as meglumine antimonate; enzymes such as alkaline phosphatase; anticoagulants such as heparin; antiallergic agents such as amoxanox; immunity activators such as muramyl dipeptide, muramyl tripeptide and TMD-66 (Japanese Patent Laid-Open Publication No. 132658/1982); and nonprescription drugs such as propranolol and glutathione.

The following Examples and Experiments further illustrate the present invention in detail. In the following Examples and Experiments, sometimes, the polyoxyethylene derivative is abbreviated, for example, the compound (I) wherein X is stearyl, n is 2 and Y is $SO_3Na$ is abbreviated as stearyl $OPOE_2SO_3Na$.

EXAMPLE 1

Dipalmitoyl phosphatidylcholine (DPPC) (225 mg), distearoyl phosphatidylcholine (DSPC) (25 mg) and stearyl $OPOE_2SO_3Na$ (25 mg) were dissolved in a 1 : 1 mixture of chloroform and isopropyl ether (90 ml) in a 1-liter beaker. To the solution was added a solution of cisplatin (CDDP) in physiological saline (1 mg/ml) (14 ml) previously prepared to have the same osmotic pressure as that of physiological saline, and the mixture was emulsified in a bath-type ultrasonic shaker (manufactured by Laboratory Supplies Co., N. Y.) to prepare a W/O type emulsion. Irradiation of ultrasonic wave was conducted for 20 minutes. The organic solvent was distilled off from the emulsion thus obtained with a rotary evaporator at 60° C. under reduced pressure to obtain REV. The degree of vacuum of the evaporator was high at the beginning, and controlled so as to avoid bumping by reducing the degree of vacuum as evaporation of the organic solvent. Then, a small amount of the residual organic solvent in REV was further distilled off by blowing nitrogen gas. The REV obtained was adjusted to 14 ml by adding a suitable amount of physiological saline, and the resultant was filtered through 1.2 micron filter (Acrodisc, Gelman) and dialyzed against physiological saline solution using a dialysis membrane (Spectrapor, Spectrum Medical) for 24 hours to obtain the liposome encapsulating CDDP of the present invention.

EXAMPLES 2 to 13

According to the same manner as that described in Example 1, the liposome compositions of the present invention were prepared by using the formulations shown in Table 1 in the same manner as that in Example 1.

TABLE 1

| Example No. | Polyoxyethylene Derivative (I) | | | | Encapsulated Drug | DPPC (mg) | DSPC (mg) |
|---|---|---|---|---|---|---|---|
| | X | n | Y | Added amount (mg) | | | |
| 1 | stearyl | 2 | $SO_3Na$ | 25 | CDDP | 225 | 25 |
| 2 | cetyl | 2 | $SO_3Na$ | 25 | CDDP | 225 | 25 |
| 3 | stearyl | 3 | $SO_3Na$ | 25 | CDDP | 225 | 25 |
| 4 | cetyl | 3 | $CH_2CO_2Na$ | 25 | CDDP | 225 | 25 |
| 5 | stearyl | 2 | $CH_2CO_2Na$ | 25 | CDDP | 225 | 25 |
| 6 | stearyl | 2 | $SO_3Na$ | 12.5 | CDDP | 225 | 25 |
| 7 | stearyl | 2 | $SO_3Na$ | 37.5 | CDDP | 225 | 25 |
| 8 | stearyl | 2 | $SO_3Na$ | 75 | CDDP | 225 | 25 |

TABLE 1-continued

| Example No. | Polyoxyethylene Derivative (I) | | | Encapsulated Drug | DPPC (mg) | DSPC (mg) |
|---|---|---|---|---|---|---|
| | X | n | Y Added amount (mg) | | | |
| 9 | stearyl | 3 | SO$_3$Na  25 | CDDP | 175 | 75 |
| 10 | stearyl | 2 | SO$_3$Na  12.5 | CDDP | 175 | 75 |
| 11 | cetyl | 3 | CH$_2$CO$_2$Na  25 | CDDP | 175 | 75 |
| 12 | stearyl | 2 | CH$_2$CO$_2$Na  25 | CDDP | 125 | 125 |
| 13 | stearyl | 2 | CH$_2$CO$_2$Na  25 | CDDP | — | 250 |

EXAMPLE 14

According to the same manner as that described in Example 13, the liposome composition of the present invention encapsulating CDDP was prepared except that egg yolk phosphatidylcholine (Egg PC) was used instead of DSPC.

EXAMPLE 15

According to the same manner as that described in Example 1, the liposome composition of the present invention encapsulating CDDP was prepared except that stearyl OPOE$_{10}$CH$_2$COONa was used instead of stearyl OPOE$_2$SO$_3$Na.

EXAMPLE 16

According to the same manner as that described in Example 1, the liposome composition of the present invention encapsulating CDDP was prepared except that stearyl OPOE$_{20}$CH$_2$COONa was used instead of stearyl OPOE$_2$SO$_3$Na.

EXAMPLE 17

According to the same manner as that described in Example 1, the liposome composition of the present invention encapsulating CDDP was prepared except that lauroyl OPOE$_2$CH$_2$SO$_3$Na was used instead of stearyl OPOE$_2$SO$_3$Na.

EXAMPLE 18

According to the same manner as that described in Example 1, the liposome composition of the present invention encapsulating CDDP was prepared except that lauroyl OPOE$_3$CH$_2$SO$_3$Na was used instead of stearyl OPOE$_2$SO$_3$Na.

EXAMPLE 19

According to the same manner as that described in Example 1, the liposome composition of the present invention encapsulating CDDP was prepared except that alkyl OPOE$_3$CH$_2$COONa (Nikkol NES-203-27, manufactured by Nikko Chemical KK, Tokyo) was used instead of stearyl OPOE$_2$SO$_3$Na.

EXAMPLE 20

According to the same manner as that described in Example 5, the liposome composition of the present invention encapsulating 5-fluorouracil (5-FU) was prepared except that 200 µg/ml of 5-FU was used instead of CDDP.

EXAMPLE 21

According to the same manner as that described in Example 5, the liposome composition of the present invention encapsulating 9-mercapto-9-deoxymaytansin (TAC805) was prepared except that 500 µg/ml of TAC805 was used instead of CDDP.

EXAMPLE 22

According to the same manner as that described in Example 5, the liposome composition of the present invention encapsulating cytosin arabinoside (Ara-C) was prepared except that 500 µg/ml of Ara-C was used instead of CDDP.

EXAMPLE 23

According to the same manner as that described in Example 5, the liposome composition of the present invention encapsulating mitomycin-C (MMC) was prepared except that 200 µg/ml of MMC was used instead of CDDP.

EXAMPLE 24

According to the same manner as that described in Example 5, the liposome composition of the present invention encapsulating daunomycin was prepared except that 1 mg/ml of daunomycin was used instead of CDDP.

EXAMPLE 25

According to the same manner as that described in Example 5, the liposome composition of the present invention encapsulating bischloroethylnitrosourea (BCNU) was prepared except that 500 µg/ml of BCNU was used instead of CDDP.

EXAMPLE 26

According to the same manner as that described in Example 5, the liposome composition of the present invention encapsulating chloroethylcyclohexylnitrosourea (CCNU) was prepared except that 500 µg/ml of CCNU was used instead of CDDP.

EXAMPLE 27

According to the same manner as that described in Example 5, the liposome composition of the present invention encapsulating human interleukin-2 (IL-2) was prepared except that 308 µg/ml of IL-2 was used instead of CDDP.

EXAMPLE 28

According to the same manner as that described in Example 9, the liposome composition of the present invention encapsulating CDDP was prepared except that 50 mg of stearyl OPOE$_2$CH$_2$CO$_2$Na was used instead of 25 mg of stearyl OPOE$_2$SO$_3$Na, encapsulating rate: 41.5%.

EXAMPLE 29

According to the same manner as that described in Example 9, the liposome composition of the present invention encapsulating CDDP was prepared except that 50 mg of stearyl OPOE$_5$CH$_2$CO$_2$Na was used instead of 25 mg of stearyl OPOE$_2$SO$_3$Na, encapsulating rate: 48.1%.

EXAMPLE 30

According to the same manner as that described in Example 9, the liposome composition of the present invention encapsulating CDDP was prepared except that 50 mg of stearyl OPOE $CH_2CO_2Na$ was used instead of 25 mg of stearyl OPOE $SO_3Na$, encapsulating rate: 29.3%.

EXAMPLE 31

According to the same manner as that described in Example 9, the liposome composition of the present invention encapsulating CDDP was prepared except that 50 mg of stearyl $OPOE_{15}CH_2CO_2Na$ was used instead of 25 mg of stearyl $OPOE_2SO_3Na$, encapsulating rate: 23.4%.

EXPERIMENT 1

According to the same manner as that described in Example 1, a control liposome composition was prepared except that stearyl $OPOE_2SO_3Na$ was not added. Likewise, according to the same manner as that described in Example 1, liposome compositions encapsulating CDDP were prepared except that the additives shown in Table 2 were used instead of stearyl $OPOE_2SO_3Na$. These liposome compositions were used as samples in the experiments hereinafter.

TABLE 2

Liposome samples containing polyoxyethylene derivatives other than those of the present invention

| Samples | Additives (Amount: 25 mg) |
|---|---|
| 1 (control) | without additive |
| 2 | $POE_2$ cetyl ether |
| 3 | $POE_{20}$ cetyl ether |
| 4 | $POE_{40}$ cetyl ether |
| 5 | $POE_2$ mono stearate |
| 6 | $POE_{10}$ mono stearate |
| 7 | $POE_{40}$ mono stearate |

In Table 2, the symbol, for example, $POE_2$ cetyl ether represents $H\text{-}(OCH_2CH_2)\text{-}O\text{-}cetyl$.

EXPERIMENT 2

The liposome compositions prepared in the above Examples 1 to 13 and Samples 1 to 7 shown in Table 2 were used and encapsulating rate (Note 1) of CDDP and stability (Note 2) after storage at 4° C. for one month were evaluated to obtain the results shown in Table 3. As seen from the results of Table 3, the liposome compositions of the present invention have equal or higher encapsulating rates in comparison with that of the control liposome composition (Sample 1) and are stable after storage for a long period of time. On the other hand, the liposome compositions obtained by addition of the POE derivatives having no negative charges (Samples 2 to 7) show low drug encapsulating rates, i e., less than $\psi$ time that of the control liposome composition.

Note 1: The amount of encapsulated CDDP in the liposome was calculated by subtracting the amount of unencapsulated CDDP from the total amount of CDDP used in the production of the composition. The amount of unencapsulated CDDP was determined by diluting the liposome composition 20 times with physiological saline and filtering the composition through a filter (centresult), further diluting the filtrate with distilled water and measuring the amount of platinum by atomic-absorption spectroscopy (Hitachi: F7000). The total amount of CDDP content was determined by directly diluting the above diluted sample 20 times with water and measuring the platinum concentration by atomic-absorption spectroscopy.

Note 2: The stability was determined by measuring the concentration of CDDP encapsulated in the liposome.

TABLE 3

Encapsulating rate and stability of liposome composition

|  | Encapsulating Rate (%) | Stability (4° C., 1M) (%) |
|---|---|---|
| Example 1 | 39.5 | 98.5 |
| Example 2 | 44.3 | 99.2 |
| Example 3 | 30.7 | 99.3 |
| Example 4 | 28.4 | 99.5 |
| Example 5 | 30.3 | 99.6 |
| Example 6 | 20.3 | 99.7 |
| Example 7 | 18.2 | 98.0 |
| Example 8 | 24.5 | 94.5 |
| Example 9 | 23.9 | 99.0 |
| Example 10 | 20.9 | 98.8 |
| Example 11 | 22.9 | 98.8 |
| Example 12 | 31.2 | 99.7 |
| Example 13 | 28.9 | 99.4 |
| Sample 1 | 25.1 | 96.7 |
| Sample 2 | 9.8 | ND |
| Sample 3 | 5.5 | ND |
| Sample 4 | 6.1 | ND |
| Sample 5 | 6.8 | ND |
| Sample 6 | 10.6 | ND |
| Sample 7 | 5.8 | ND |

EXPERIMENT 3

Using the liposome compositions prepared in the above Examples 1 to 13 and Samples 1 to 7, aggregation precipitation rate of the liposome was evaluated by measuring dispersion of the liposome with times by light scattering (Note 3). The results are shown in Table 4. As seen from Table 4, the liposome composition without addition of any POE derivative (Sample 1) and the liposome compositions obtained by addition of the POE derivative having no negative charge (Sample 2) show aggregation within a short period of time, while the liposome compositions of the present invention maintain the dispersed state for a long period of time.

Note 3: After the liposome composition was diluted about 100 times with physiological saline and thoroughly stirred, the resultant was placed in a sample cuvette and measured for light scattering by submicron analyzer (manufactured by Coulter) and decrease of intensity of scattering after standing for a given time was measured based on scattering immediately after stirring defined as 100 to estimate dispersibility of the liposome composition (intensity of scattering decreases upon causing aggregation precipitation).

TABLE 4

Dispersibility of liposome after one week

|  | Dispersibility (%) |
|---|---|
| Example 1 | 98 |
| Example 2 | 98 |
| Example 3 | 81 |
| Example 4 | 99 |
| Example 5 | 87 |
| Example 6 | 61 |
| Example 7 | 100 |
| Example 8 | 87 |
| Example 9 | 102 |
| Example 10 | 87 |
| Example 11 | 71 |
| Example 12 | 85 |

TABLE 4-continued

| Dispersibility of liposome after one week | |
|---|---|
| | Dispersibility (%) |
| Example 13 | 82 |
| Sample 1 | 17 |
| Sample 2 | 84 |
| Sample 3 | 20 |
| Sample 4 | 63 |
| Sample 5 | 87 |
| Sample 6 | 83 |
| Sample 7 | 96 |

EXPERIMENT 4

Figure 2:
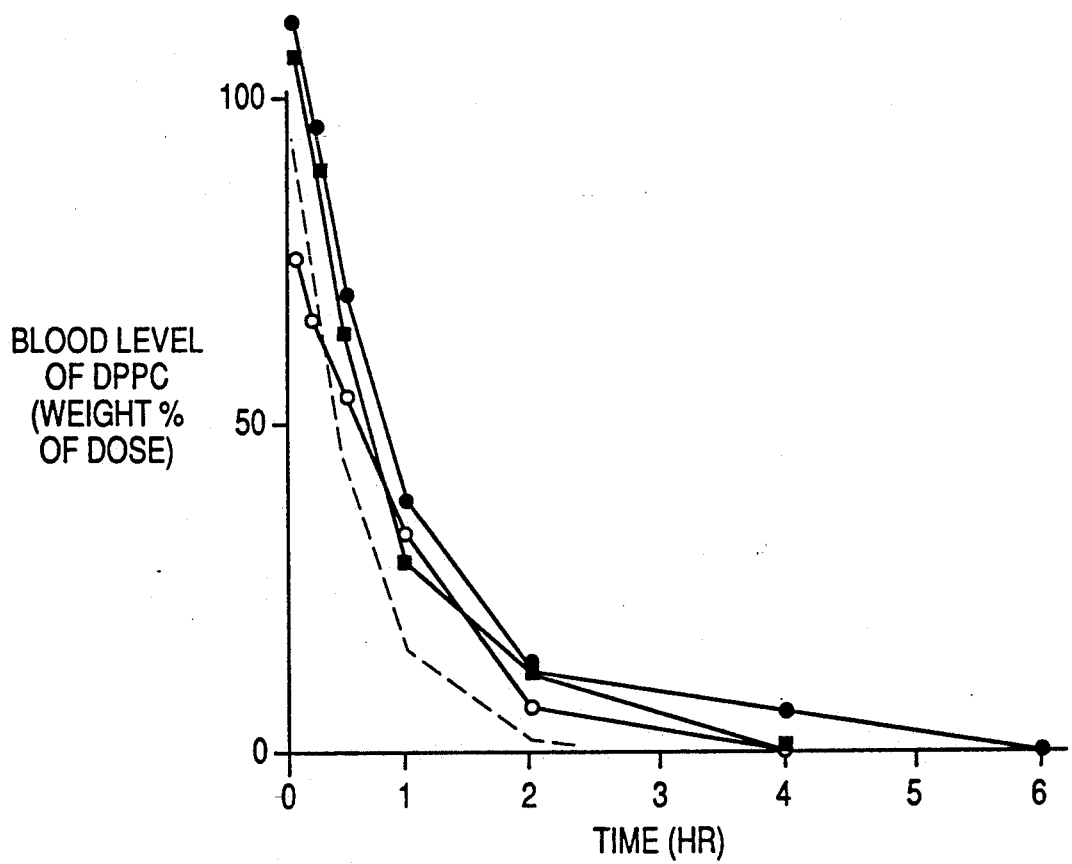
FIG. 2 shows change of blood level of lipid after administration of the liposome compositions shown in Experiment 4 hereinafter, wherein O, ■, ■ and --- represent the liposome compositions of Examples 6, 7 and 8 as well as Sample 1 hereinafter, respectively.

After administration of the liposome composition (1 ml) prepared in the above Example 1 to a rat, change of blood concentration of lipid (Note 4) was observed to obtain the results shown in FIG. 1 (Examples 2, 3, 4 and 5) and FIG. 2 (Examples 6, 7 and 8). As seen from the results of FIGS. 1 and 2, the liposome composition is retained in blood for a longer period of time in comparison with the control liposome composition containing no additive.

Note 4: The collected blood was treated with heparin, diluted 10 times with physiological saline, thoroughly stirred and centrifuged. The supernatant was separated and extracted with chloroform and DPPC concentration in the extract was quantitatively measured by HPLC (column: Bondasphere C4-100A manufactured by Waters; eluent: phosphate buffer (pH 7)/methanol(1/9); detector: showdex, refraction index analyser) to determine blood concentration of lipid.

The above results show that the liposome composition of the present invention obtained by addition of the polyoxyethylene derivative to form the lipid composition has remarkably improved dispersibility as well as high encapsulating property of a drug and stability after storage for a long period of time. Further, the liposome composition of the present invention has the characteristics of long lasting of a drug in blood when intravenously administered.

As described hereinabove, the liposome composition of the present invention has good dispersibility and high encapsulating property of a drug as well as high stability. Accordingly, it can be advantageously used as preparations for medicaments and the like.

What is claimed is:

1. A liposome composition whose liposome membrane comprises a polyoxyethylene derivative represented by the general formula:

$$X-O-(CH_2CH_2O)_n-Y \qquad (I)$$

wherein X represents an alkyl group, Y represents an anion-forming group, and n is an integer of 5 to 15, and a phospholipid selected from the group consisting of glycerophospholipid and sphingophospholipid, wherein the ratio of the phospholipid t the polyoxyethylene derivative is about 0.5 to 200 parts by weight of the polyoxyethylene derivative based on 100parts by weight of the phospholipid.

2. A liposome composition according to claim 1 wherein the anion-forming group is $-CH_2CO_2H$, $-CH_2CH_2CO_2H$, $-OSO_3H$, $-CH_2SO_3H$, $-CH_2CH_2SO_3H$, $-OPO_3H$ or a salt thereof.

3. A liposome composition according to claim 1, wherein X is $C_{5-30}$ straight or branched chain alkylcarbonyl.

4. A liposome composition according to claim 1, X is $C_{5-30}$ straight or branched chain alkyl.

5. A liposome composition according to claim 1, wherein the phospholipid is glycerophospholipid or sphingophospholipid having a saturated alkanoyl group having 12 to 20 carbon atoms.

* * * * *

UNITED STATES PATENT AND TRADEMARK OFFICE
CERTIFICATE OF CORRECTION

PATENT NO. : 5,252,336
DATED : October 12, 1993
INVENTOR(S) : KATSUMI IGA, KAZUHIRO OHKOUCHI, YASUAKI OGAWA It is certified that error appears in the above-identified patent and that said Letters Patent is hereby corrected as shown below:

At column 10, line 20, change "phospholipid t" to

--phospholipid to--.

Signed and Sealed this

Seventh Day of June, 1994

Attest:

BRUCE LEHMAN

Attesting Officer      Commissioner of Patents and Trademarks